United States Patent
Melese et al.

(10) Patent No.: US 7,477,571 B2
(45) Date of Patent: *Jan. 13, 2009

(54) METHOD FOR DETECTING VIBRATIONS IN A BIOLOGICAL ORGANISM USING REAL-TIME VIBRATION IMAGING

(75) Inventors: Philip Melese, Palo Alto, CA (US); Eric Lavelle, San Jose, CA (US); Lawrence H. Dubois, Palo Alto, CA (US); Katherine Donaldson, Santa Clara, CA (US)

(73) Assignee: SRI International, Menlo Park, CA (US)

( * ) Notice: Subject to any disclaimer, the term of this patent is extended or adjusted under 35 U.S.C. 154(b) by 158 days.

This patent is subject to a terminal disclaimer.

(21) Appl. No.: 11/351,316

(22) Filed: Feb. 7, 2006

(65) Prior Publication Data

US 2006/0209631 A1 Sep. 21, 2006

Related U.S. Application Data

(63) Continuation-in-part of application No. 10/817,116, filed on Apr. 2, 2004, now Pat. No. 7,027,353.

(60) Provisional application No. 60/460,542, filed on Apr. 3, 2003.

(51) Int. Cl.
*G01H 9/00* (2006.01)

(52) U.S. Cl. .......................................... 367/7; 73/655

(58) Field of Classification Search ................. 367/149; 73/653, 655, 656
See application file for complete search history.

(56) References Cited

U.S. PATENT DOCUMENTS

| 5,249,163 | A  | * | 9/1993  | Erickson ....................... 367/149 |
| 5,886,265 | A  | * | 3/1999  | Chatrefou ..................... 73/655 |
| 7,027,353 | B2 | * | 4/2006  | Melese et al. ................... 367/7 |
| 7,073,384 | B1 | * | 7/2006  | Donskoy et al. ............... 73/655 |
| 7,168,323 | B1 | * | 1/2007  | Discenzo ...................... 73/655 |
| 2004/0193033 | A1 | * | 9/2004  | Badehi et al. ................ 600/402 |
| 2004/0234187 | A1 | * | 11/2004 | Wong et al. ................... 385/13 |

* cited by examiner

*Primary Examiner*—Ian J Lobo
(74) *Attorney, Agent, or Firm*—Lumen Patent Firm

(57) ABSTRACT

The present invention provides a method for detecting vibration information by receiving electromagnetic radiation reflected or emitted from a biological organism at a light amplitude modulation detector array to provide real-time imaging of the target object. The detected radiation may be visible light, infrared or ultraviolet radiation, and/or of other desired frequency ranges. The detected radiation is preferably AC-coupled to isolate components relating to oscillations of the biological organism from components relating to ambient radiation, e.g. background sunlight. The isolated oscillations may then be digitized, stored, and subjected to processing such as a Fourier transform to generate outputs representative of frequencies of oscillation. This output can then be used for analysis of the target object.

18 Claims, 17 Drawing Sheets

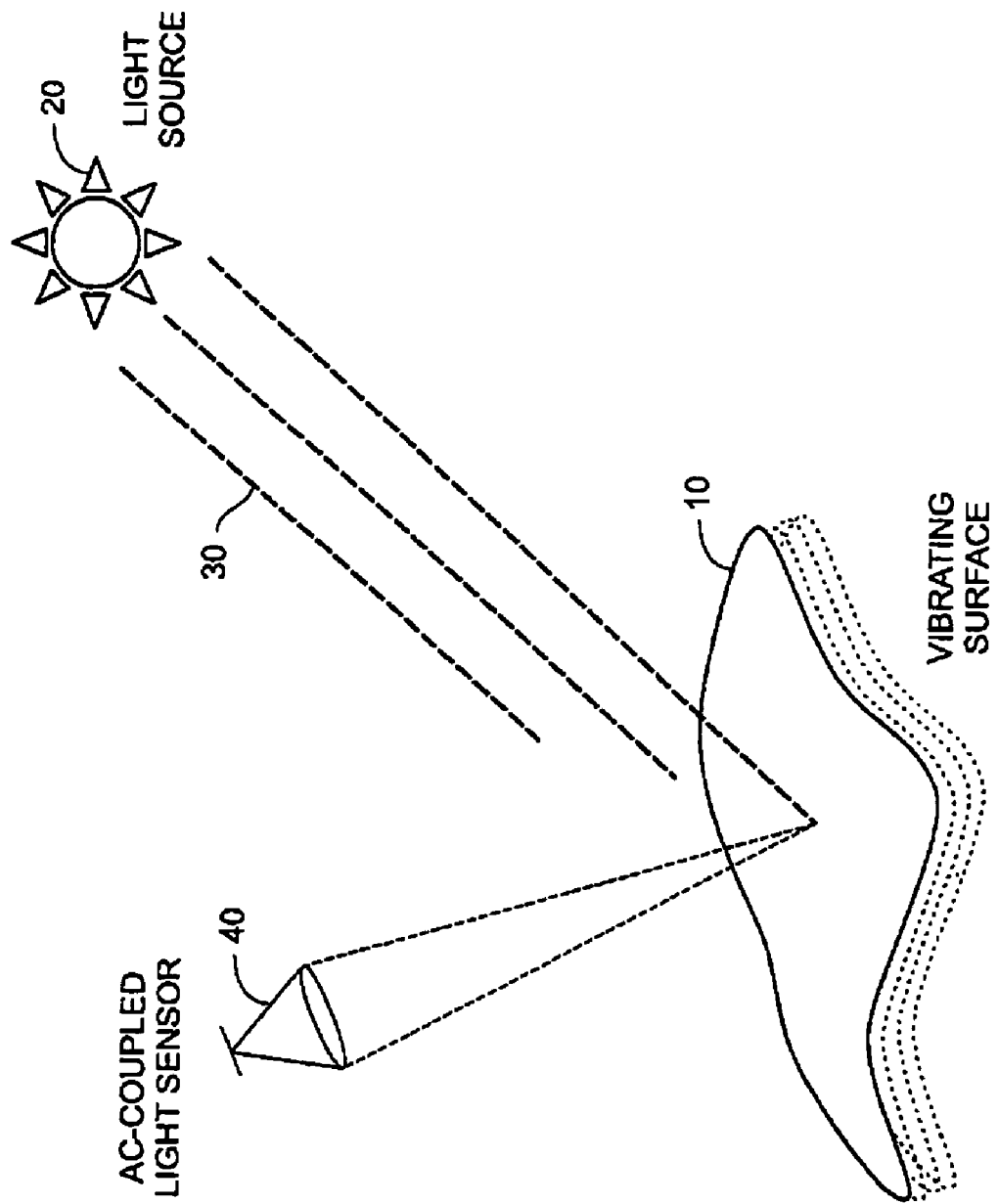

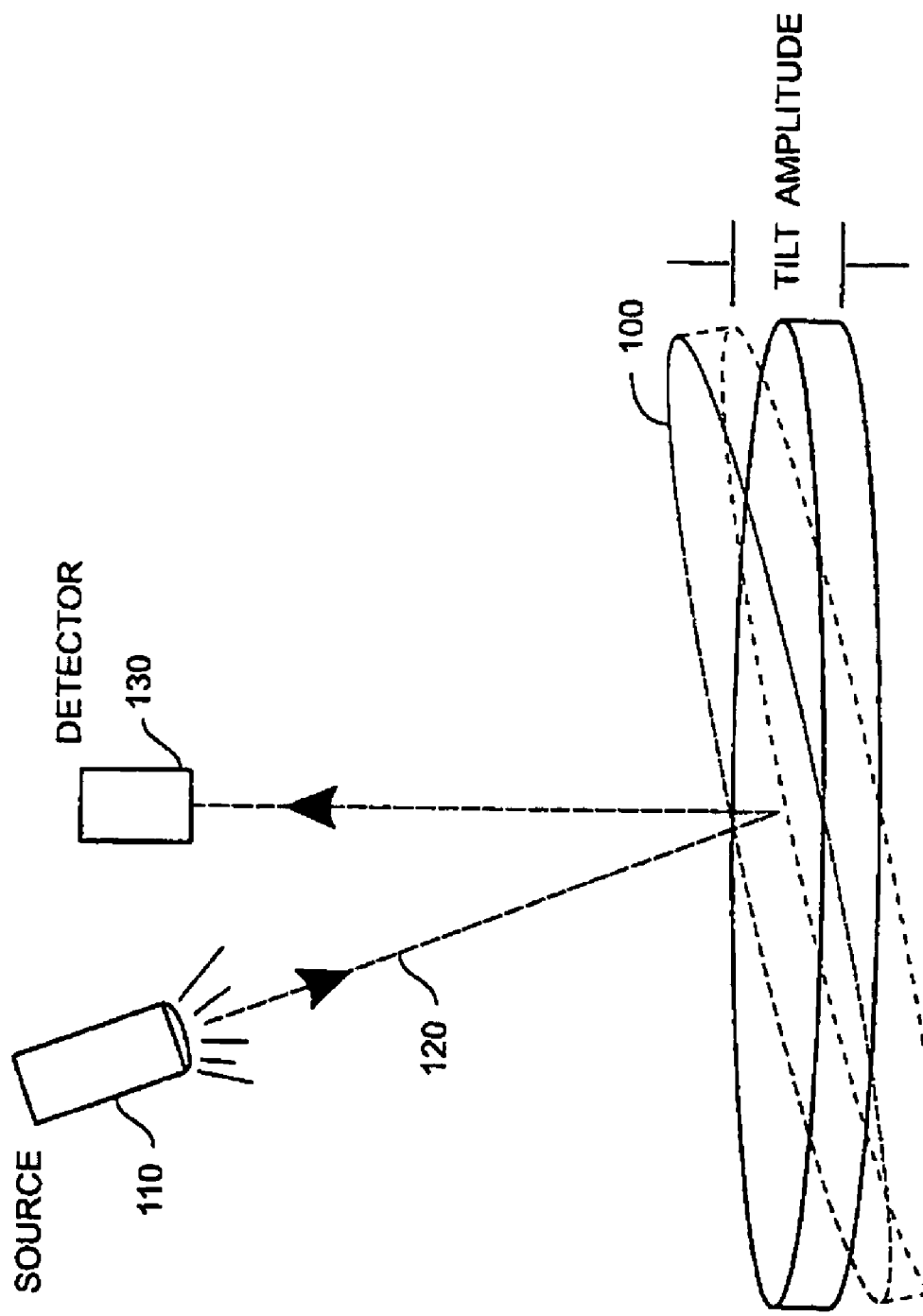
FIG._2

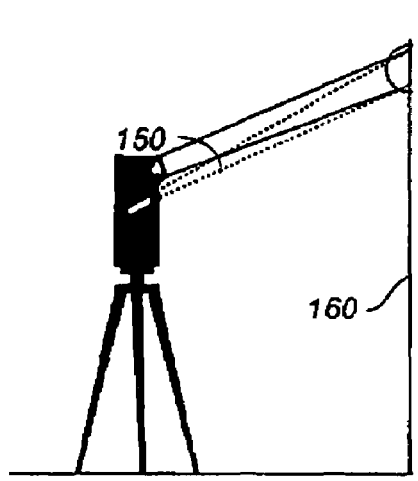 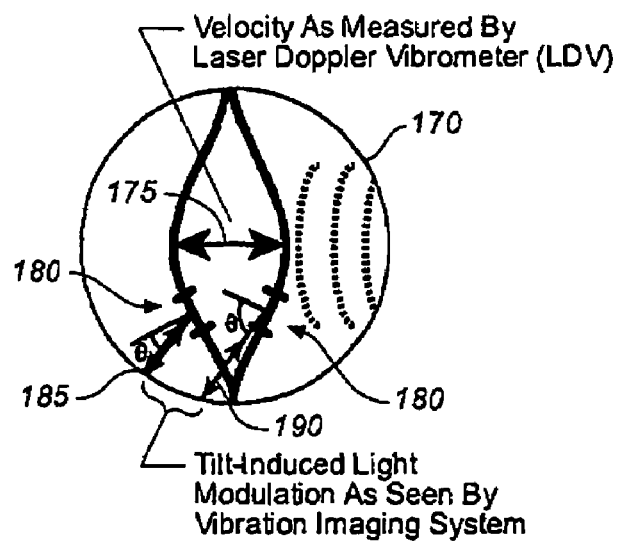
FIG._3A  FIG._3B
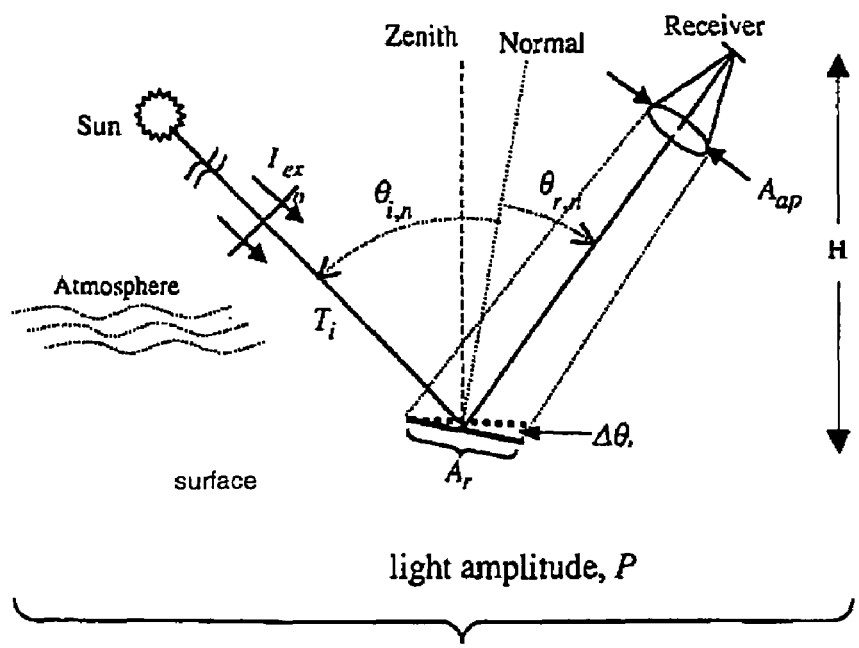
FIG._4

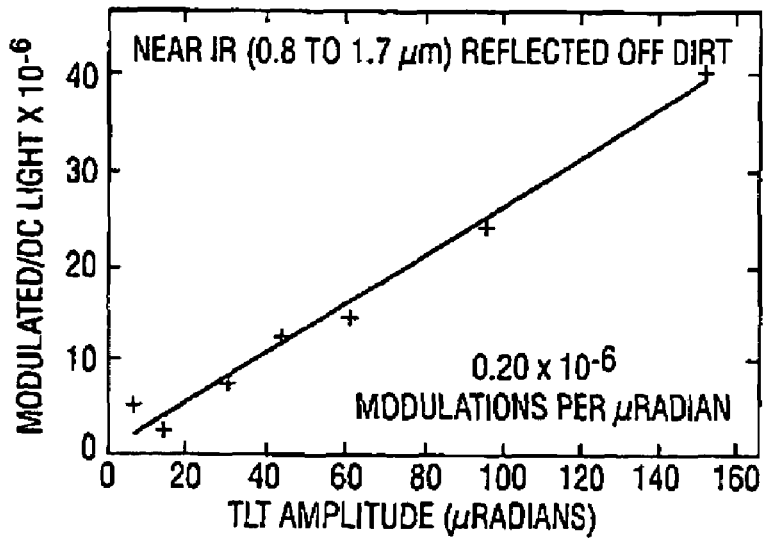
FIG._5
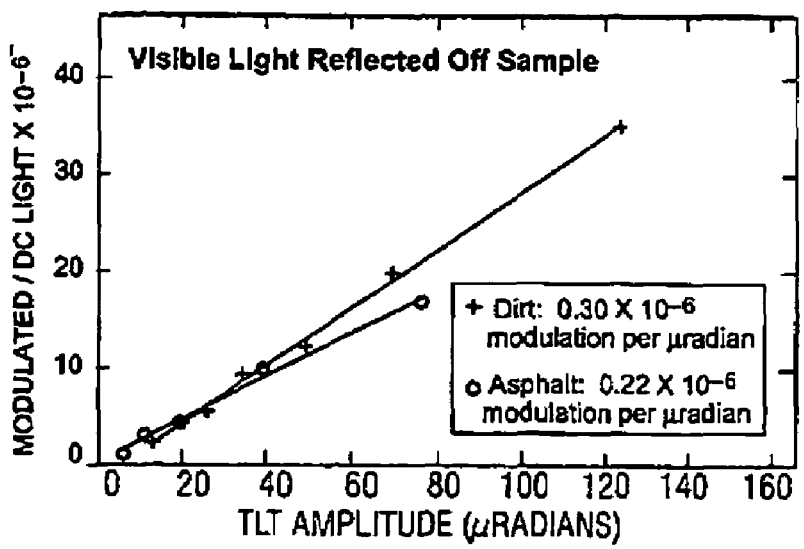
FIG._6

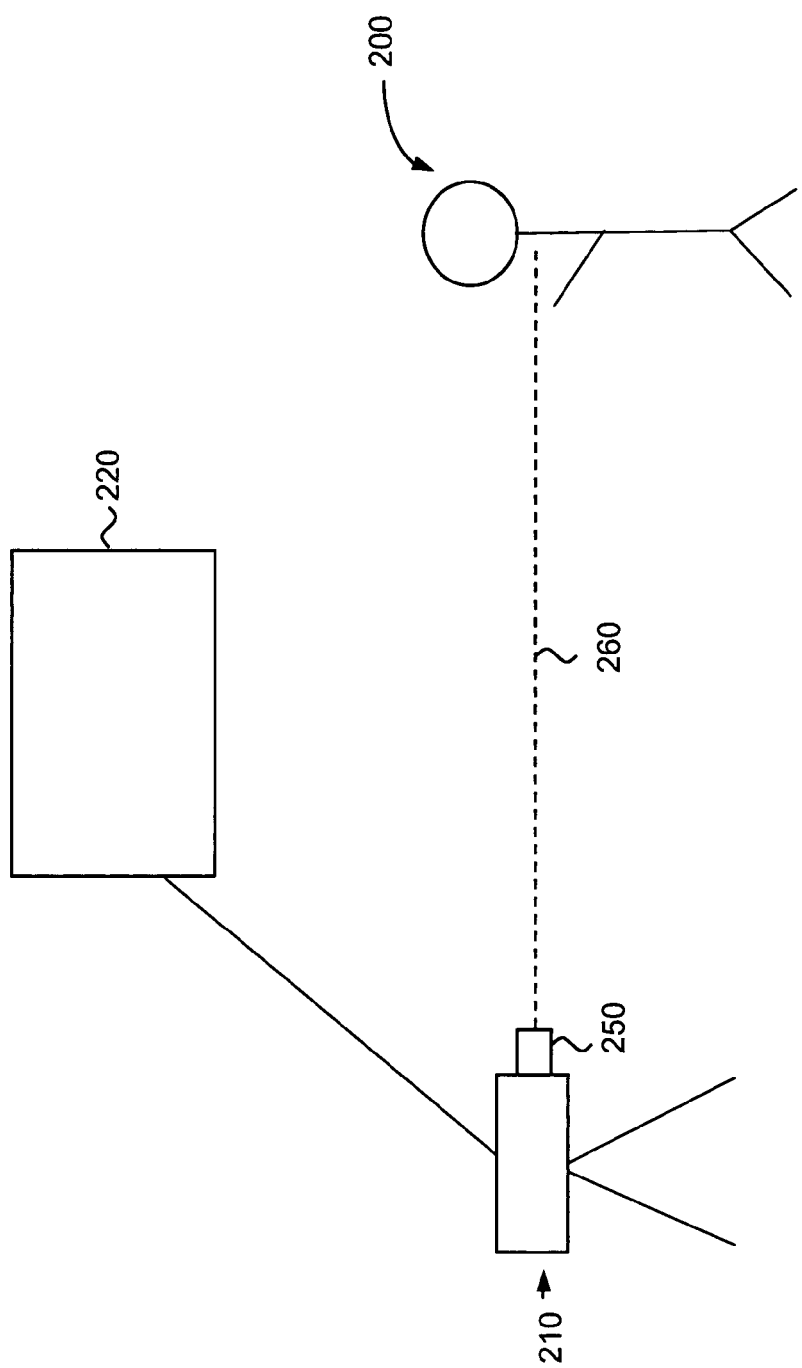
FIG._7

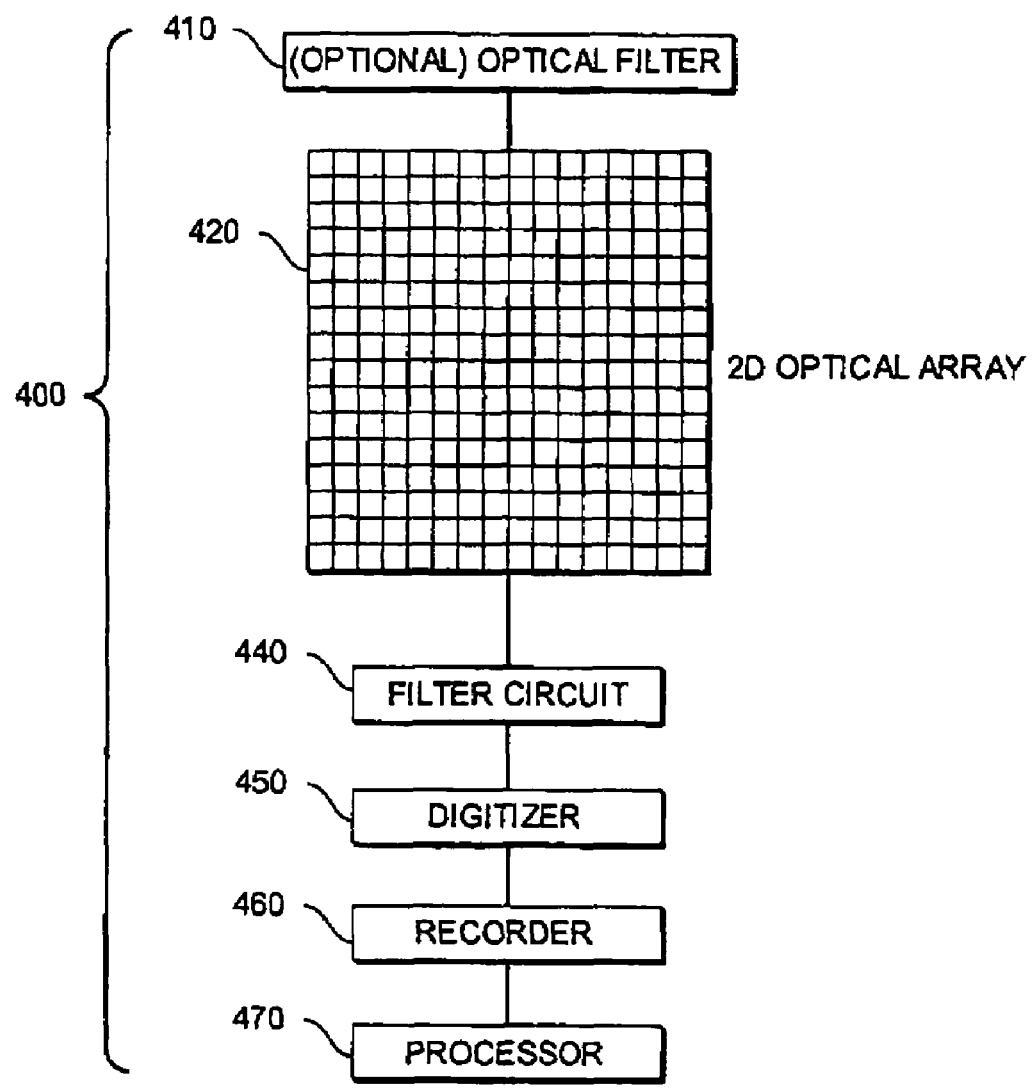
FIG._8

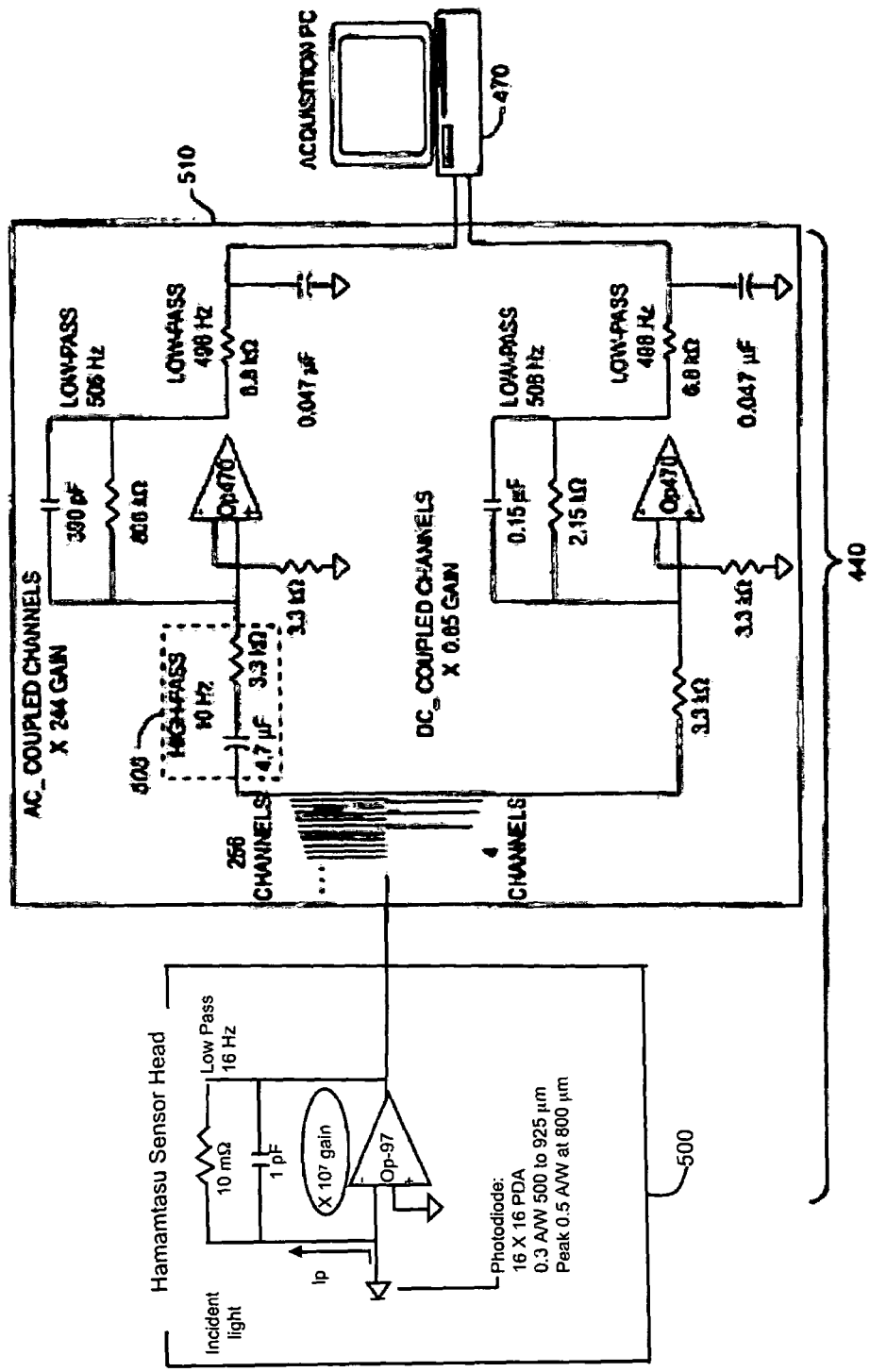
FIG._9

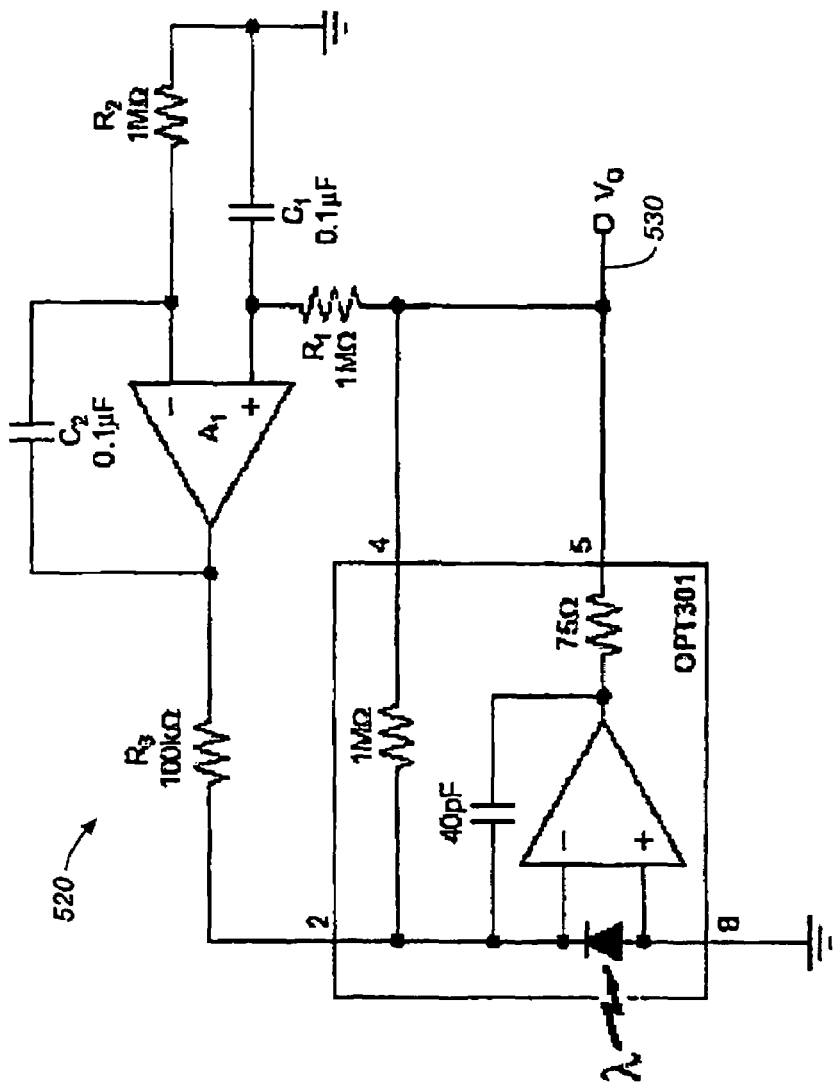
FIG._10

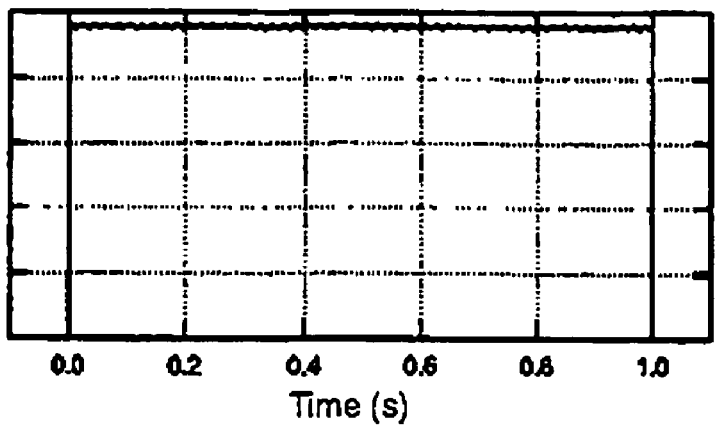
FIG._11A
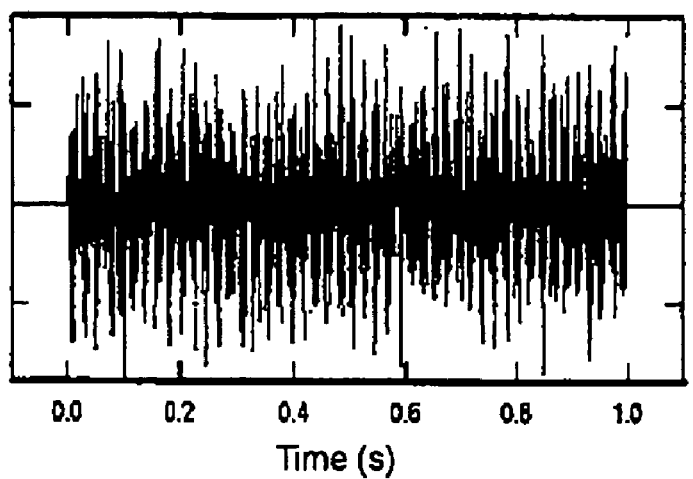
FIG._11B
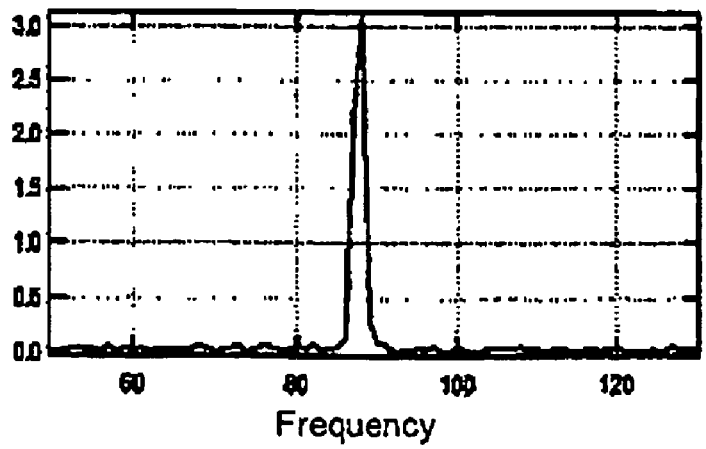
FIG._11C

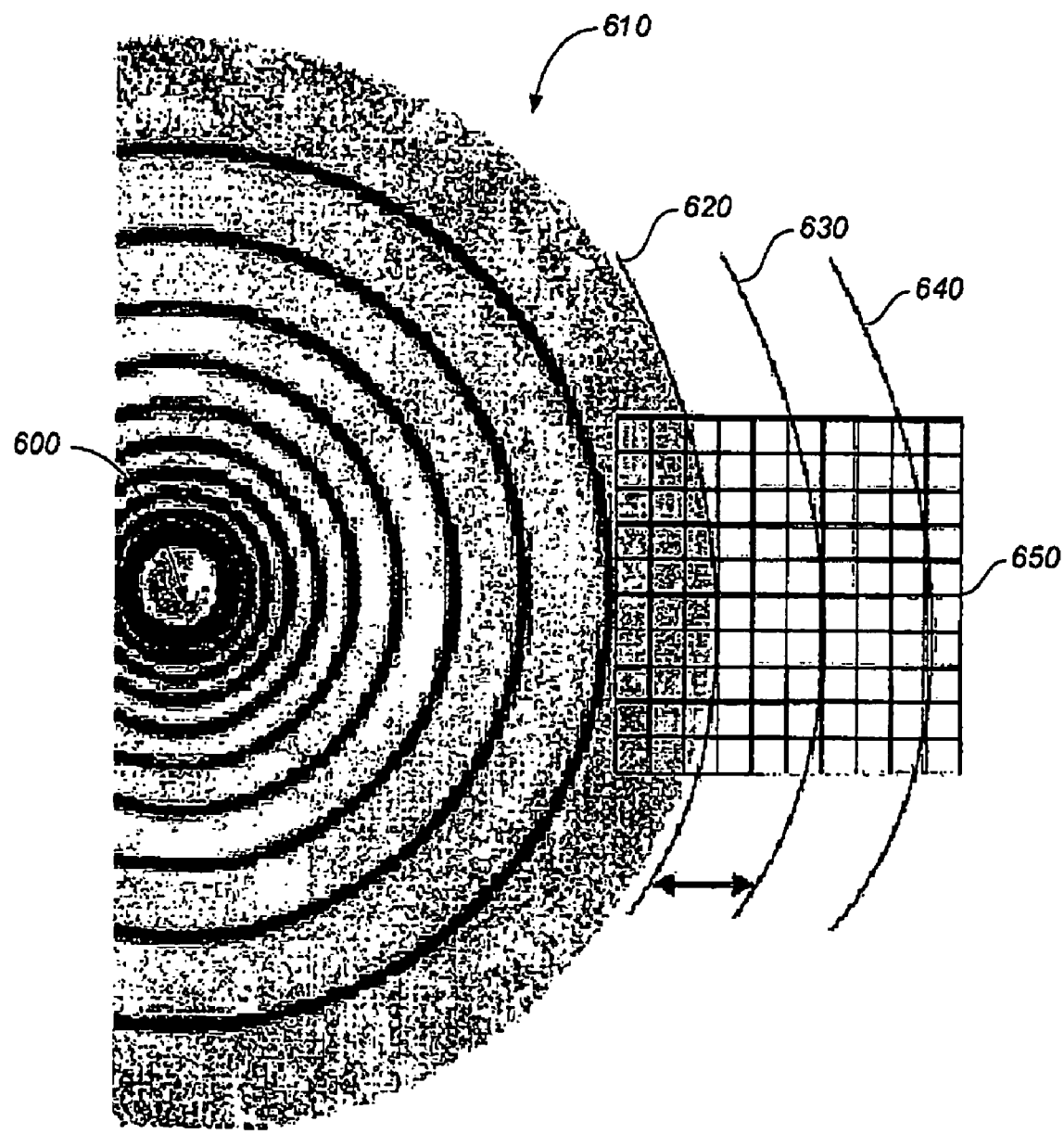
FIG._12

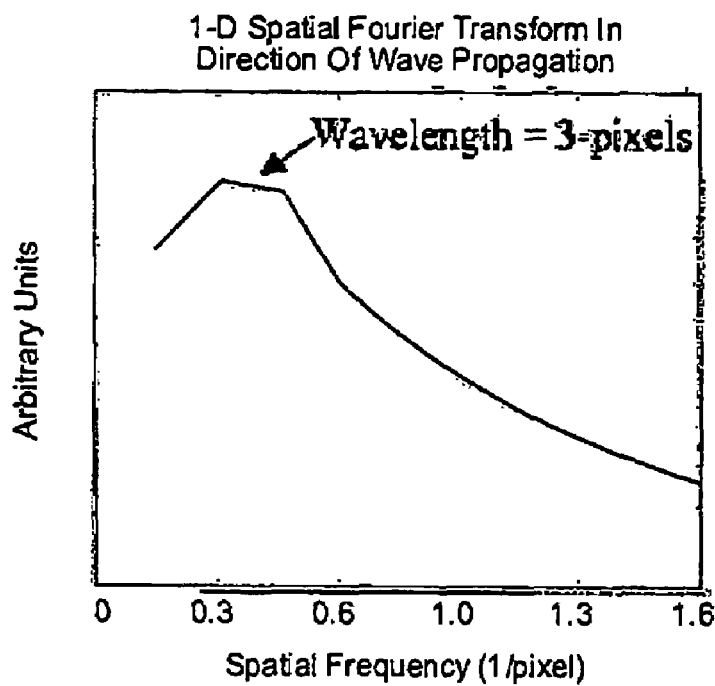
FIG._13
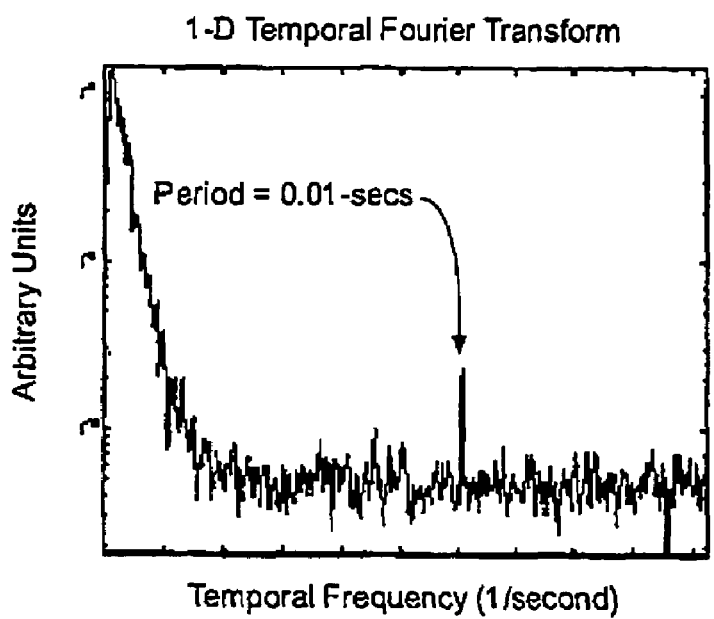
FIG._14

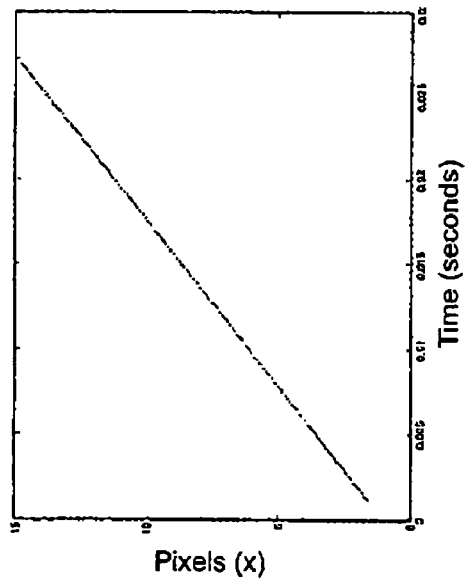
FIG._16
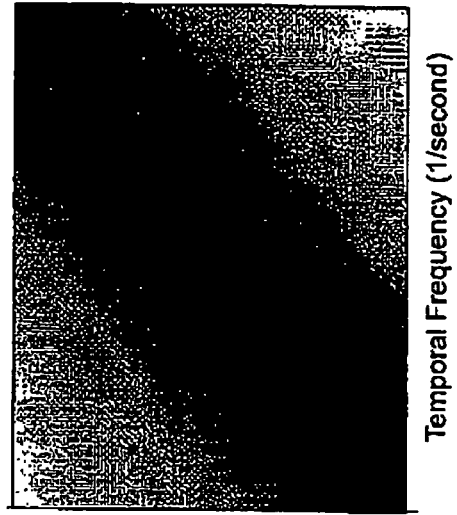
FIG._17
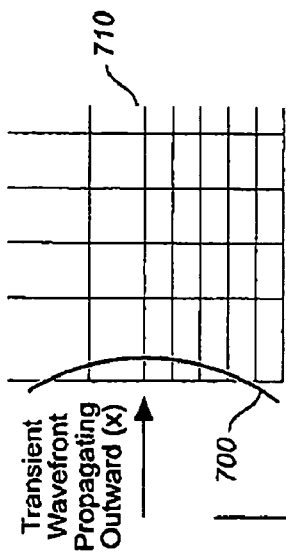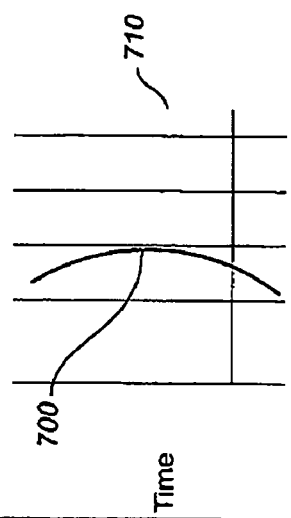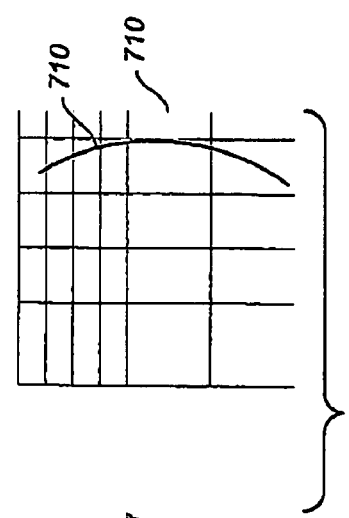
FIG._15

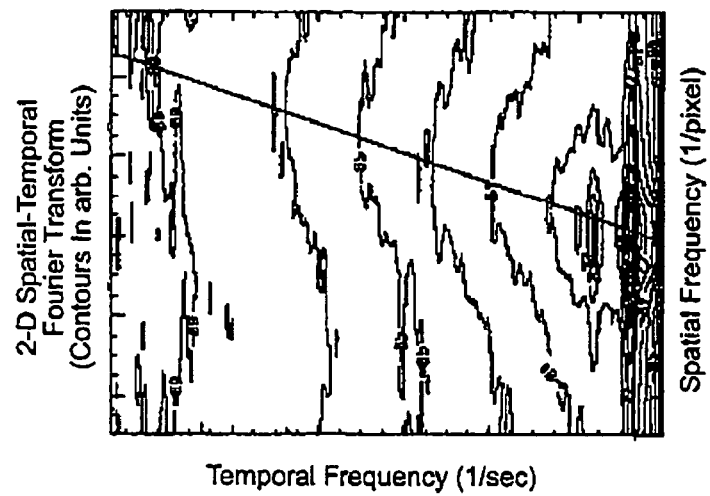
FIG._19
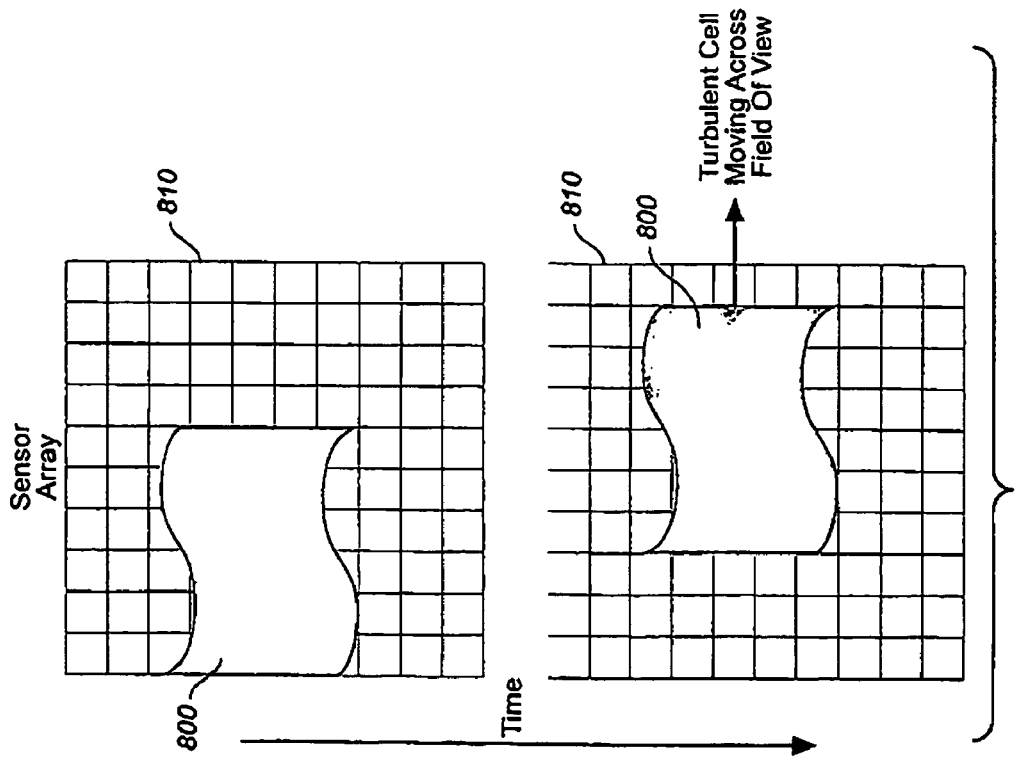
FIG._18

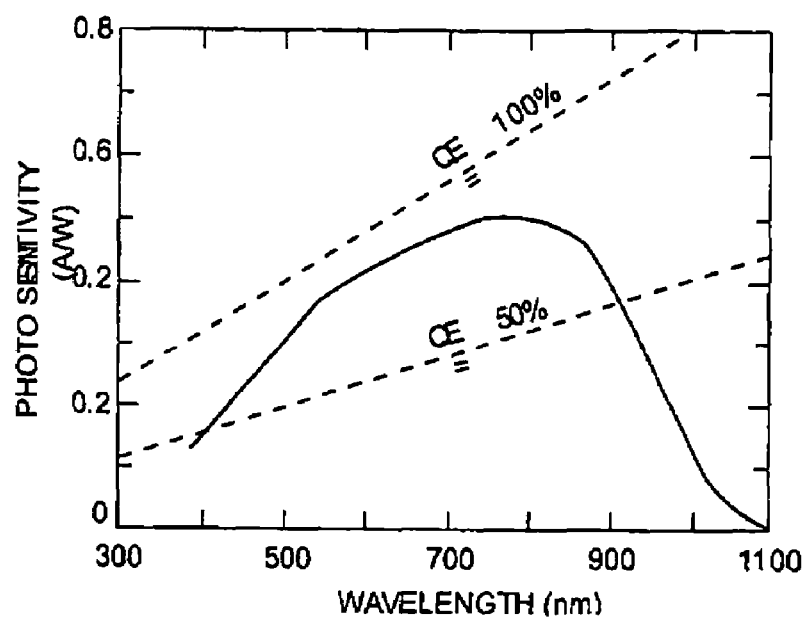
FIG._20
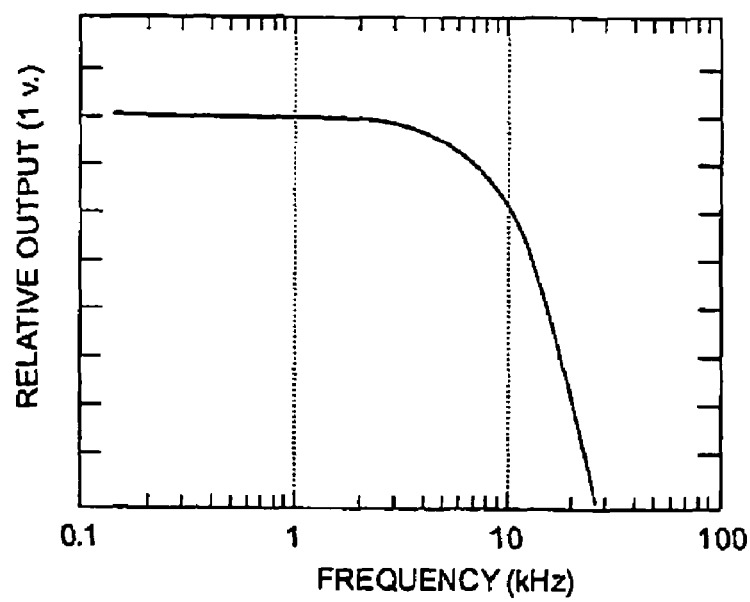
FIG._21

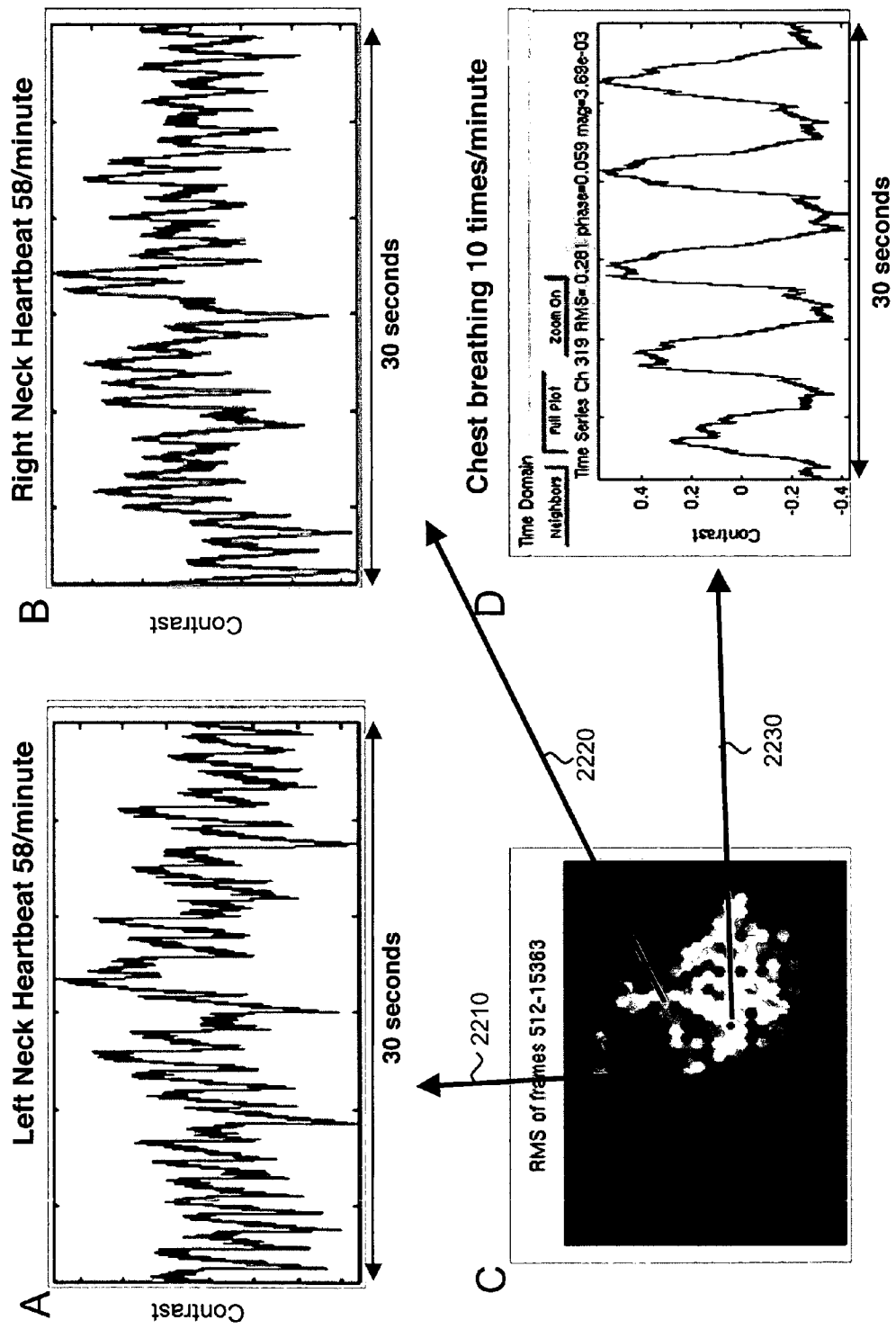
FIG._22

METHOD FOR DETECTING VIBRATIONS IN A BIOLOGICAL ORGANISM USING REAL-TIME VIBRATION IMAGING

CROSS-REFERENCE TO RELATED APPLICATIONS

This application is a continuation-in-part of U.S. application Ser. No. 10/817,116, filed Apr. 2, 2004, now U.S. Pat. No. 7,027,353, which claims priority from U.S. Provisional Patent Application No. 60/460,542 filed Apr. 3, 2003, both of which are incorporated herein by reference.

FIELD OF THE INVENTION

The present invention relates generally to detection of vibrations. More particularly, the present invention relates to methods of remotely detecting vibrations in a biological organism using real-time vibration imaging.

BACKGROUND

Various systems and methods have been used to detect biological signatures such as pulse rate, heart rate, tremor, etc. in biological organisms. Generally, these systems and methods require contact with the organism in order to function. Thus, these methods and systems can be unsuitable for applications in which contact with the organism is undesirable, such as with burn victims and in defense applications.

Laser Doppler Vibrometers can remotely measure vibrations in biological organisms, and have been used in applications such as the measurement of blood flow. However, LDVs have several drawbacks. First, they must use scanners to collect images from a large region of an organism. Second, they use lasers, which can potentially be harmful to the subject. Third, they are generally limited to measurement of small amplitude vibrations, rather than the relatively large amplitude, low frequency, vibrations that are of biological interest. Accordingly, there is a need in the art to develop a method of remotely measuring vibrations in biological organisms that can image an entire organism or region of an organism, that is safe, and that can detect relatively large amplitude, low frequency vibrations.

SUMMARY OF THE INVENTION

The present invention provides a method for detecting vibrations in a biological organism using a real-time vibration imaging system, such as described in U.S. patent application Ser. No. 10/817,116, which is incorporated by reference herein. With this method, light modulation amplitude detectors, such as a photodetector array (PDA), receive light that is reflected or emitted from regions of a biological organism. This light modulates due to vibrations in the biological organism. The vibrations may be a result of movement of, e.g., biological fluids, air, organs, tissues, muscles, or body parts. The received light is sampled at some predetermined frequency, such as between 10 Hz and 10 kHz, and is periodically stored, such as once per second, to generate a series of signals. These signals are correlated to vibrations at corresponding regions of the biological organism. The signals are then digitized and used to generate an output that represents the vibrations of the regions of the biological organism. This output may be, e.g., a visual representation of the biological organism that is correlated with the signals generated from the corresponding regions of the organism.

Preferably, oscillation information is isolated from information relating to ambient light reflected from or emitted by the biological organism by extracting the oscillation information. This extraction may be accomplished by removing at least one component representing ambient radiation in the vicinity of the organism. Preferred methods of extraction are AC-coupling, DC-rejection, or high-pass temporal filtering of the received signals. Alternatively, or in addition, the received light may be optically filtered at the light modulation amplitude detectors to remove unwanted components of ambient radiation.

Preferably, the digitized signals are processed to extract frequency information from the signals. Methods of processing include, but are not limited to, executing a Fourier transformation on the digitized signals, executing wavelet analysis of the digitized signals, and filtering the digitized signals. A preferred filtering method is match filtering.

The output and frequency information may be used to detect or measure a property of a biological organism. Examples of properties that may be detected or measured include, but are not limited to, heart rate, pulse rate, tremor, eye-blink rate, eye movement, blood oxygen level, and blood flow.

BRIEF DESCRIPTION OF THE FIGURES

The present invention together with its objectives and advantages will be understood by reading the following description in conjunction with the drawings, in which:

FIG. 1 is an illustration of light reflecting from a vibrating surface to a light sensor.

FIG. 2 is an illustration showing tilt amplitude in a vibrating surface similar to FIG. 1.

FIGS. 3A-3B show examples of basic configurations of a vibration imaging system (VIS) useful for practicing the method of the present invention.

FIG. 4 shows a more detailed geometry of a VIS useful for practicing the method of the present invention.

FIG. 5 is a graph of infrared light reflected from a sample (dirt).

FIG. 6 is a graph of visible light reflected from samples (dirt and asphalt).

FIG. 7 is an illustration of a VIS useful for practicing the method of the present invention.

FIG. 8 is a block diagram of a VIS useful for practicing the method of the present invention.

FIGS. 9-10 are schematic diagrams of electronic filters and AC- and DC-coupling channels suitable for use in a VIS useful for practicing the method of the present invention.

FIGS. 11A-11C illustrate isolation and removal of DC signals relating to ambient fight from AC oscillation signals of interest according to the present invention.

FIGS. 12-14 illustrate detection according to the present invention of wavefronts propagating from a vibrating source.

FIGS. 15-17 illustrate detection according to the present invention of a transient wavefront.

FIGS. 18-19 illustrate detection according to the present invention of a turbulent cell across a target region.

FIG. 20 is a graph illustrating a spectral response obtained using the method of the present invention in a biological setting, in which voltage-sensitive dyes may be used to produce spatial-temporal maps of electrical activity in biological systems.

FIG. 21 is a graph illustrating frequency response obtained using the method of the present invention in the setting of FIG. 20.

FIGS. 22-23 show examples of vibratory signals that may be obtained according to the method of the invention.

DETAILED DESCRIPTION OF THE INVENTION

Figure 23:
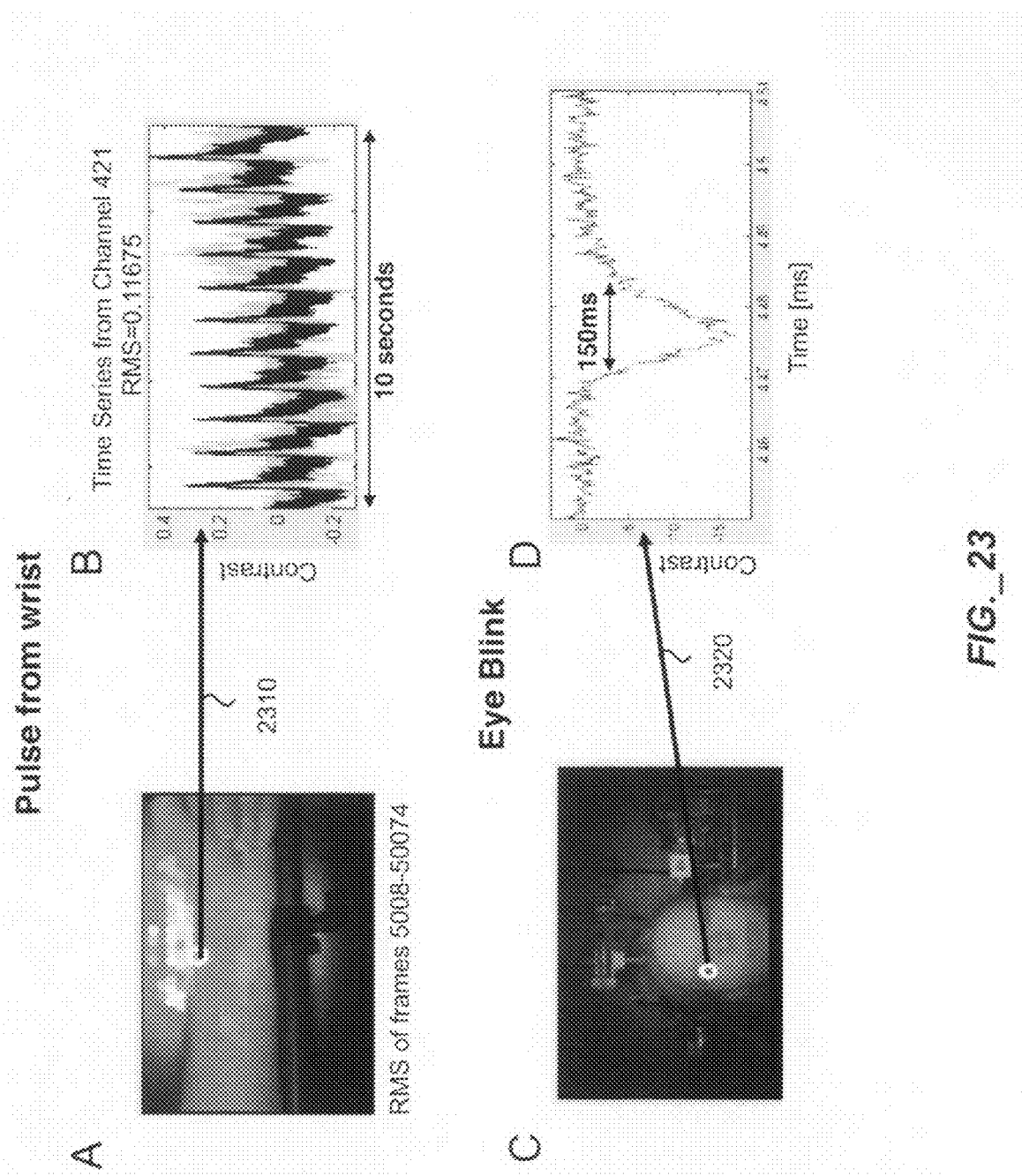

A simple example of a vibrating surface 10 is shown in FIG. 1, wherein light source 20 emits electromagnetic radiation 30, which reflects from the surface 10 and at least in part is detected at a light sensor 40. The light source 20 may in general refer to any suitable source of electromagnetic radiation, and the radiation 30 may be of any of a number of ranges of wavelengths, e.g. visible light, infrared (IR), ultraviolet, etc. Thus, when the term "light" or "optical" is used herein, it will be understood that any desired frequency or range of frequencies of electromagnetic radiation may be used, and the light source may be naturally occurring (e.g. the sun) or artificial (e.g. a laser or a lamp). The sensor 40 is accordingly configured to detect the wavelengths of interest, and as discussed below includes circuitry and software as needed to capture, process, analyze and display frequencies, relative magnitudes and phase information of the detected light substantially simultaneously.

Although the present invention will be described in terms of light that is reflected from a biological organism, it is equally applicable to detection of light that is emitted (e.g. due to fluorescence or thermal IR emission), and thus when reflection is mentioned it may be taken also to refer to emission, fluorescence, etc. In addition, reference to a detected "signal" should be taken to refer to any such radiation.

The term "light signal" as used herein may be taken to refer to any amplitude modulated light signal resulting from movements or vibrations of an object or surface, and in particular embodiments described herein include electromagnetic radiation of any suitable wavelength that is reflected, emitted, etc. from an object undergoing motion as detected by a VIS.

In general, the term "logic" as used herein refers to electronic circuitry, processor-based systems or subsystems or other hardware, software and/or firmware as appropriate to implement the teachings of the present invention, and where any one of these (e.g. a circuit or a processing program or routine) is referred to, it should be understood that other hardware, software or firmware may be used to equivalently implement the same functions or features.

Regions of a biological organism that are subject to shocks, oscillations or forces that otherwise cause them to move may set up characteristic vibrations, and in particular may vibrate at frequencies that are useful for analysis, e.g. to determine properties of a biological organism. As discussed below, the present invention is applicable to imaging and processing of signals detected from regular oscillations or from single-impulse or other nonrepetitive motions of a region of a biological organism. Thus, where any of vibrations, oscillations, pulses or other motions are referred to herein, it will be understood that any combination of such motions (or lack of motion, for particular regions of a biological organism) may be present.

When the term "image" or "imaging" is used herein, it may refer either to logical representation of signals that can be correlated to corresponding regions of the biological organism, and/or it may refer to an actual visual, display or printed representation of the signals, with or without a correlation with a representation of corresponding regions of the biological organism.

Theoretical Concepts of the Invention

Vibration imaging (detection, processing and analysis) according to the invention utilizes the known phenomenon in optics that characteristics of light as reflected from a surface depend upon the angles of incidence and reflection of the light (i.e. incoming and outgoing angles) relative to the surface. The angular dependence of reflectance from a surface is called the bidirectional reflectivity distribution function (BRDF). An additional signal contribution comes from the purely geometrical tilt-induced change in flux of the incident collimated light on an imaged surface. In real-life complex objects, sharp transitions in reflectance and shadows can amplify the induced contrast in the light signal.

Vibratory motions modulate this surface tilt, in turn modulating the angles and thus the reflectance. The net result is that the vibratory motion modulates the amplitude of light reflected from the surface. Vibration imaging according to the present invention detects the modulation of light reflected from many small areas on the surface simultaneously, and is therefore a measure of surface motion (or lack of motion, for regions undergoing no vibration) in terms of tilt. The optical "contrast," defined in one embodiment as the tilt-induced change in light amplitude (light modulation) divided by the total light amplitude (the ambient or DC light), is substantially proportional to the surface tilt for small angle changes. Other definitions of "contrast" as used herein may be suitable, with the common concept being that the tilt-induced change in light amplitude is detected and used to determine the vibration characteristics as described.

FIG. 2 illustrates a vibrating (or otherwise moving) surface 100, where light source 110 transmits light 120 to the surface 100. The light 120 reflects from the surface to light amplitude modulation detector 130, and is modulated depending upon the tilt amplitude of the surface 100.

FIGS. 3A-3B illustrate in greater detail a basic configuration of a VIS, showing a light amplitude modulation detection apparatus 150 aimed at a surface 160, with enlargement 170 detailing a local perturbation of the surface. The tangential vector 175 represents the motion a laser Doppler vibrometer (LDV) (velocity) or an accelerometer would measure. The change in tilt of the small line segment 180 of the surface 160 denotes the field of view of a single pixel, which causes the light reflection angle ($\theta$) to change from that shown as arrow 185 to that shown as arrow 190 and then back again as the surface vibrates. The change in reflectivity with this angle is described in greater detail below. The modulation in the light intensity from a given "unit" area 180 as in FIG. 3B is measured by one of the pixels in the image produced by a vibration imager of the invention. This "unit" area 180 may vary in size with different lenses or fields of view of a system according to the invention.

FIG. 4 shows a general deployment geometry for a VIS useful for practicing the method of the present invention. A light source (which may be collimated, such as sunlight) impinges on a surface of a biological organism at an incident (subscript "i") angle of $\theta_{i,n}$, where subscript "n" indicates the angle with respect to the surface normal. The angle $\theta_{i,n}$ changes with motion of the biological organism. Similarly, the reflected light is viewed by the receiver (subscript "r") at an angle $\theta_{r,n}$ with respect to the normal.

The light source may as indicated be collimated, and/or it may be coherent (such as laser radiation), or it may be neither. For interior applications, an active collimated illuminator can be used, which has the advantage that it provides control over the light angles. The illuminator light can be broadband and visible, like sunlight, or it can be narrow-band (such as a near-IR laser). Photodiodes or other photodetectors of suitable sensitivity should be selected, depending upon the light source.

The light source should also be of sufficient intensity to limit shot noise and overcome background ambient light, and preferably have minimal temporal modulation, i.e. variation in the intensity of the light source over time. Battery-powered spotlights are suitable for many applications.

In prior systems, the use of an accelerometer or LDV entails measuring a single spot on the target surface at a time, so in order to spatially sample a surface (i.e. produce a vibration image), the LDV must be scanned or an array of accelerometers would have to be used. In the system useful for practicing the present invention, by way of contrast, an array of simultaneous images is generated from, e.g., 256 contiguous (or alternatively, at least partly contiguous and possibly partly separated in space) target spots, thus providing a full-scene imaging sensor for analysis of the target biological organism.

Equation A-1 below gives the light amplitude P at the receiver in terms of the incident irradiance I, atmospheric transmission T, the BRDF b, an imaged surface element area $A_r$, the receiver aperture $A_{ap}$, the receiver height above the ground H, and the angular dependences.

(Atmospheric transmission effects $T_i$ can be ignored for these short ranges.)

$$P = I_{exo} \cdot (T_{atm,0})^{sec\theta_{i,z}} \cdot \cos\theta_{i,n} \cdot b(\theta_{i,n}, \theta_{r,n}) \cdot \frac{A_r \cos\theta_{r,n} A_{ap}}{(H/\cos\theta_{r,z})^2} \cdot (T_{H,0})^{sec\theta_{r,z}} \quad (A\text{-}1)$$

Equation A-2 shows how the Vibration Imaging signal, the optical contrast $\Delta/\langle P \rangle$ is proportional to the surface tilt $\Delta\theta_t$, i.e., the change in angle of the subtended area $A_r$ as the imaged surface vibrates. The proportionality has a geometrical dependence $\tan\theta_{i,n}$ on the incident light angle and terms arising from the partial derivatives of the BRDF b with respect to the incident and reflected light angles.

$$\frac{\Delta P}{\langle P \rangle} = \left[\tan\theta_{i,n} - \frac{1}{b(\theta_{i,n}, \theta_{r,n})} \cdot \left(\frac{\partial b}{\partial \theta_{i,n}} + \frac{\partial b}{\partial \theta_{r,n}}\right)\right] \cdot \Delta\theta_t \quad (A\text{-}2)$$

In the laboratory, data were collected using a controlled tilt-platform and various illumination and sensor angles, as shown in FIG. 2. The resulting plots of FIGS. 5 and 6 shows the substantially linear relationship between the measured optical contrast and the measured (using two displacement sensors) surface tilt for dirt and asphalt surfaces at different illumination wavelengths. This setup was used to verify that equation A-2 accurately describes the dependence of the optical contrast on the illumination and receiver angles.

The signal in units of contrast per radian of tilt is typically on the order of 1/radian or $10^{-6}/\mu$radian. This can also be derived from equation A-2 by assuming a Lambertian reflector (i.e., b=constant), for which the contrast per radian of tilt ($\Delta P/\langle P \rangle/\Delta\theta_t$), reduces to $\tan\theta_{i,n}$, which also gives 1/radian at 45° from the normal and 6/radian at 80° from the normal.

The above results thus indicate that the modulated light signal is substantially linearly dependent upon the tilt magnitude of the target surface.

Systems Suitable for Practicing the Invention

FIG. 7 is a diagram of a VIS that could be used to perform the method of the present invention. In this example, a target object of interest is a human 200, which has vibrations of biological interest, representing pulse rate, heart rate, breathing rate, tremor, eye blink, eye movement, eye-blink rate, blood oxygen level, blood flow, etc. A detector array is included in a camera 210 or other detecting apparatus, and communicates (by a network connection, a wireless channel, or the like) to a processor-based system 220 coupled to a display and user input apparatus such as keyboard and/or mouse, trackball or other digital input devices, not shown. A preferred processor-based system is a laptop-based acquisition system. An example of a camera suitable for the invention is a one with a 464-element photodiode array (PDA), though larger or smaller arrays may also be used. As an alternative to photodiodes, the individual detectors may be CMOS devices or other opto-electronic devices as appropriate. Preferably, the camera also includes a CCD imager, to allow standard images to be acquired along with PDA images.

A lens 250 focuses light 260 reflected from the biological organism onto the photodiodes of the PDA, and the photodiodes convert the light into electric currents in a conventional manner. These currents are filtered and amplified using standard electronic techniques, as described in greater detail below, and the outputs from the photodiodes are then digitized and recorded (i.e. digitally stored) at some predetermined frame rate, e.g. at a sample rate of 5 kHz. Other frame rates may be used, and the frame rate may be altered when desired, including dynamically altered in real time based upon predetermined criteria and/or user input.

In general, in a VIS useful for practicing the invention, the processor or processing module will be configured to generate processed outputs relating to the detected amplitude modulated light signals at predetermined regular time intervals, where the time intervals are larger than time intervals corresponding to the predetermined sample rate. For instance, a sample rate of 1 kHz and a processing interval of 1 second may be used, a sample rate of 1 GHz and a processing interval of 0.1 millisecond (for a moving target, with very fast circuitry in the processing module), etc. The predetermined sample rate may itself be variable for different applications.

Lens 250 may be a conventional zoom or telescopic lens, allowing the user to isolate or focus in on a particular region of interest in the target object or scene.

Detector logic configured to carry out the conversion, digitization, filtering and amplification as described herein may be included in the camera 210, or may constitute a logic module separate from the primary detection optics and electronics, e.g. a logic module coupled to an output of a video-camera and coupled to an input of the system 220, or integrated into the system 220.

In one embodiment, the photodiodes of the PDA are AC-coupled to the amplifiers of the detector array and the signals are filtered prior to digitization, so that only changes (deltas) detected at each pixel or element of the PDA are recorded or stored. Storing only the deltas can greatly increase the dynamic range sensitivity of the system.

For regions of the biological organism that are stationary, no signal (except perhaps noise) will be recorded. For parts of the biological organism that are moving, changes in signals from the corresponding photodiodes of the array (which correspond to pixels in the resulting image) will be registered as fluctuations in the biological organism.

Those changes in the received signals will in general have associated frequencies and amplitudes due to the vibrations of regions in the biological organism corresponding to the respective photodiodes (or pixels). Thus, an apparatus according to FIG. 7 is configured to spatially map the amplitudes and frequencies of vibrations in the biological organism. Collecting data from all pixels simultaneously or substantially simultaneously allows detection and analysis of spatial and phase relationships of the vibration over the entire biological organism or an area of interest in the biological organism. ("Substantially simultaneous" data collection may be defined as data collection for different pixels within a time interval that results in correlation errors for the data for the different pixels no larger than some acceptable or predetermined limit.) The number of pixels or target spots can readily be expanded.

The interrogated area of the biological organism (including the "unit" area corresponding to a single pixel and the total imaged area) depends on the geometry of the biological organism and the nature and setting of the lens in front of the sensor head, which may be a commercial off-the-shelf (COTS) lens. By using a standard zoom lens, the area of interest and the pixel size on the surface may be changed easily and dynamically. In an embodiment with a 16×16 photodiode (pixel) array in the sensor head, the interrogated area is divided into 256 subregions all of which are independently and simultaneously monitored for frequency and amplitude of tilt.

In one embodiment of an actual implementation of a VIS useful for implementing the present invention, the sensitivity of the vibration imager, in terms of tilt angle, has been determined to be about 1 µradian (0.00017°), which is approximately the angle subtended by a 1-meter high stick viewed from a distance of 1000 km. To support such a fine resolution, the dynamic range of the sensor is preferably about 24 dB, which can be achieved by:

(a) employing photodiodes with excellent inherent dynamic range;
(b) AC coupling to eliminate the large DC component due to the ambient light level;
(c) digitizing the resulting AC signal with high precision, e.g. 16-bit precision or greater; and/or
(d) coherently integrating the signal over time (currently over about 1-second intervals).

The modulated-to-ambient light ratio (i.e., the contrast sensitivity) for this actual embodiment, which is of interest here, was on the order of $10^{-5}$ to $10^{-6}$. A contrast sensitivity of at least about $10^{-4}$ (and ideally, $10^{-5}$, $10^{-6}$-or better) is desirable in ambient-light settings for usually expected vibrational amplitudes, for which the modulation of the incipient light due to the vibrations may be on the order of only a few ten-thousandths of a percent (roughly 0.0001% to 0.001%).

FIG. 8 is a block diagram of a generalized circuit that may be used to implement the present invention. An optical filter 410 may be placed in front of the detector array or module 420 (which, as indicated above, may be incorporated into or coupled to a conventional camcorder, camera, or the like) to reduce reception at the detector module of undesired frequencies of light. The detector module 420 includes a detector array as described above, and its output is subject to analog processing, such as by being passed through a filter circuit 440 (discussed below), and thereafter digitized by a conventional analog-to-digital converter 450. A digital recorder 460 stores the digitized signals, and they are provided to a processor 470 for further processing and analysis.

FIG. 9 is a schematic diagram of a circuit suitable for incorporation into filter circuit 440 of FIG. 8. In this embodiment, a sensor head such as that available from Hamamatsu K.K. (headquartered in Hamamatsu City, Japan—see http://www.hamamatsu.com) with a suitable photodiode array may be used. A single photodiode channel 500 of a Hamamatsu sensor currently in use is shown in FIG. 9.

In this case, a high-pass filter 505 is used to increase the dynamic range of the frequency range of interest. An amplifier/filter board 510 includes both an AC-coupled channel and a DC-coupled channel for each pixel, i.e. for 256 channels in the embodiment discussed above. By filtering out the ambient light signal—which appears in the channels as DC (nonoscillating) signals—prior to digitizing it, the AC signals due to vibrations of the target scene can be effectively isolated and the dynamic range improved. Thus, the circuitry of the amplifier board 510 filters the signals output from the sensor head to separate the AC components of the signals from the DC components, and these components are then amplified and digitized. Each amplified photodiode AC output is independently digitized and passed to the computer or other processor-based system for storage and processing.

FIG. 10 illustrates an alternative circuit 520 for filtering out the DC component to isolate the AC signal. In this embodiment, a DC restoration is performed within the first stage transimpedance amplifier coupled to the photodiode. Circuit 520 is effectively a combination of high-pass filter 505 and circuit 500. In one embodiment, circuit 520 replaces both circuit 500 and the circuitry on the board 510, though its output 530 is passed through a second-stage amplifier (similar to the DC-coupled channel of board 510) before being input to the system 470.

One embodiment of AC coupling according to the invention is illustrated in FIGS. 11A-11C. FIG. 11A depicts the overall signal for a given pixel, showing a small AC oscillation riding on a large DC offset. In FIG. 11B, the DC portion of the signal has been substantially removed by the use of AC coupling (i.e. high-pass filtering), thus effectively isolating the AC component of the signal, which is then amplified. In FIG. 11C, the signal shown in FIG. 11B has been subjected to Fourier transform—e.g. FFT (fast Fourier transform) for real-time processing—or other frequency analysis, revealing the spectral content of the modulated signal. For the signal in this example, a resonant frequency response of about 87 Hz is visible in the resulting graph.

The simultaneous capture of light amplitude modulated signals across the detector array focused on the target region provides the flexibility of determining the nature of the vibratory phenomena giving rise to those signals, and in addition the channel-by-channel treatment and analysis of those signals, as described below. This detection and signal processing on the basis of individual pixels relating to target "unit" spots provides a powerful analytical tool.

Analysis of Oscillating and Transient Signals

FIGS. 12-19 illustrate application of a system of the invention to the detection and analysis of signals relating to oscillating and transient signals.

Periodic Signals

FIG. 12 is an illustration of an impulsive source 600 which generates an acoustic oscillation generally 610, which includes multiple generally periodic wavefronts 620-640, etc., which propagate outwards from the source 600, e.g. at a velocity of approximately 300 m/s. In a detector apparatus according to the invention, a sensor array 650 receives reflected light from a region of interest, in this case covering a region in which three wavefronts 620-640 are at least partially represented. Surface distortions are caused in the target region by the vibratory wave, which result in tilts in the surface that modulate the reflected light, as discussed above. A VIS according to the invention provides two-dimensional spatial information of this tilt as a function of time, effectively projected onto the pixel array.

In the far-field (relatively distant from the point of impact), the surface wave achieves substantially steady-state propagation, such that the disturbance has a relatively uniform effective wavelength.

In this example, the successive wavefronts are separated by about three pixels each, and thus one wavelength may be regarded as the distance in the target region corresponding to three pixels. If, for instance, each pixel represents a one-square-meter area, then the wavelength in this example is three meters. If the waves are propagating with a velocity of 300 m/s, then the frequency of the oscillation is 300 m/s divided by 3 meters, or 100 $\sec^{-1}$ (100 Hz).

This is illustrated in FIG. 13, where the spatial frequency of the detected signals is represented in a one-dimensional spatial Fourier transform in the direction of wave propagation, showing a peak at a frequency of about 0.3 $pixel^{-1}$, i.e. a wavelength of about 3 pixels.

When a temporal or time-domain Fourier transform is performed in the direction of propagation (e.g. the x-direction in FIG. 12), a peak will represent an effective period in seconds. FIG. 14 illustrates the result of such a Fourier transform in this example, and shows a peak at period of 0.01 seconds, i.e. a frequency of 100 Hz.

Transient Signals

FIG. 15 is a sequence of diagrams illustrating a transient wavefront 700 propagating outward in the x-direction, superimposed on a detector array 710 which is used to detect reflected light from a target region subjected to a shock wave or the like resulting in formation of the wavefront 700. "Transient" is used here to indicate a disturbance that does not have a readily discernable or substantially uniform period or oscillation. In this case, the circuitry and processing logic associated with the detector array detects a signal traversing array pixels over time, as indicated by the graph of FIG. 16, wherein the slope of the pixels-vs.-time curve (or line) represents the velocity of the transient wavefront in pixels per second.

If a two-dimensional Fourier transform is carried out on the detected signals (after filtering, digitizing, etc. as discussed above), the resulting data or graph will show a correlation between the spatial frequency (here, 1/pixel in the direction of propagation) and the temporal frequency (here, 1/second or 1 Hz), assuming the same wavefront velocity (300 m/s) and target region area corresponding to each pixel (1 meter square) as in the example of FIGS. 12-14. Such a result is illustrated in FIG. 17, which depicts an ideal, uniform distribution of spatial and temporal frequencies. A diagonal correlation in temporal and spatial frequencies is evidence of the velocity of the signal. A two-dimensional Fourier transform can also be applied to the propagating wavefront example of FIGS. 12-14.

The data depicted in FIGS. 16 and 17 can be extrapolated into three dimensions (two spatial and one temporal), such that velocity vector across the array (with both x and y components) can be determined.

FIG. 18 illustrates the situation when a disturbance such as an atmospheric scintillation moves as a turbulent cell 800 across a target region of a vibration imaging array 810 according to the invention. This type of phenomenon may be analyzed according to the well-known "frozen flow" model. Although the cell 800 may be determined by some systems to be a source of noise (or random signals), a system according to the invention correctly determines that the cell is an optical disturbance moving in space (e.g. in the x-direction here) and time, similar to the transient wavefront example discussed above.

FIG. 19 is a plot of actual data generated using a method according to the invention, wherein a two-dimensional spatial-temporal Fourier transform has been performed on the data. The plot of FIG. 19 shows power density (as contours) vs. the spatial and temporal frequency. The presence of a path in the contours (marked by the diagonal line) indicates an effective velocity (in pixels/second), and is consistent with the frozen-flow model. If there were no spatial-temporal correlation, then the plot of FIG. 19 would simply show concentric circular contours about the origin, i.e. the zero spatial (1/pixel) and zero temporal (1/second) point.

Scintillations may be considered a noise source, particularly for the long-range sensing of vibrations. However, the ability to characterize and understand these sources leads to the ability to digitally or analytically filter such scintillations out of the data, and thus isolate other phenomena of interest.

Detection of Vibrations in Biological Organisms

FIG. 20 is a graph illustrating the spectral response of a VIS as used in a biological setting, in which voltage-sensitive dyes may be used to produce spatial-temporal maps of electrical activity in biological systems, such as the heart, neurons, etc. In this case, in a wavelength range of about 450 nm to 900 nm, the photo sensitivity is between a Q.E. (quantum efficiency) of 50% and 100%, with 100% being an ideal response. Thus, a broad spectral response can be achieved. FIG. 21 is a graph illustrating the frequency response in the same biological setting, and shows that a substantially flat frequency response is achieved for vibrations out to several kHz.

FIGS. 22-23 show examples of vibratory signals that may be obtained according to the method of the invention. If a root-mean-square (RMS) light modulation signal is calculated for each pixel's data, and the resulting values are visually superimposed on an image of the target object, where the RMS values are correlated spatially with the correct spots in the target object, images such as those shown in FIG. 22C, FIG. 23A, and FIG. 23C result, where lighter pixels indicate a greater amount of vibration. In FIG. 22C, RMS for a hexagonal PDA was superimposed on a CCD image. FIG. 22 A, B, and D show graphs of contrast versus time recorded from individual pixels, indicated by the bases of arrows 2210, 2220, and 2230, respectively, where contrast is defined as the tilt-induced change in light amplitude (light modulation) divided by the total light amplitude (the ambient or DC light). The light amplitude modulation signals represent left neck heartbeat, right neck heartbeat, and chest breathing, respectively.

FIG. 23A shows RMS for a pixel array superimposed on a CCD image of an arm. Arrow 2310 points to light amplitude modulation signals obtained from a pixel located in the wrist (FIG. 23B), and represents wrist pulse rate. FIG. 23C shows RMS for a pixel centered on an eye. Arrow 2320 points to light amplitude modulation signals from that pixel (FIG. 23D), which represents an eye blink. Both FIGS. 23B and 23D illustrate optical contrast versus time.

Other vibratory signals that may be detected and measured according to the invention include eye movement, blood oxygen level, and blood flow (not shown). Eye movement may be detected by measuring the change in light reflected off the eye. Blood flow may be inferred by measuring pulse propagation across the arm, for example, from elbow to hand through fingers. This in turn could reveal high blood pressure, hardening of the arteries, or arterial blockage. Blood oxygen level may be determined by analyzing differences in reflection between two wavelengths of light that are sensitive to oxygenated blood, similar to the operation of a pulse oximeter.

The method of the presentation can be used to detect vibrations from distances between microns and meters. For example, heartbeat detection using this invention has been demonstrated in the infrared at distances of between 1 and 5 m.

Various sampling speeds may be used according to the present invention, on the order of 10s or thousands of frames/sec. Preferably, the sampling speed is on the order of hundreds of frames/sec.

Figure 24:
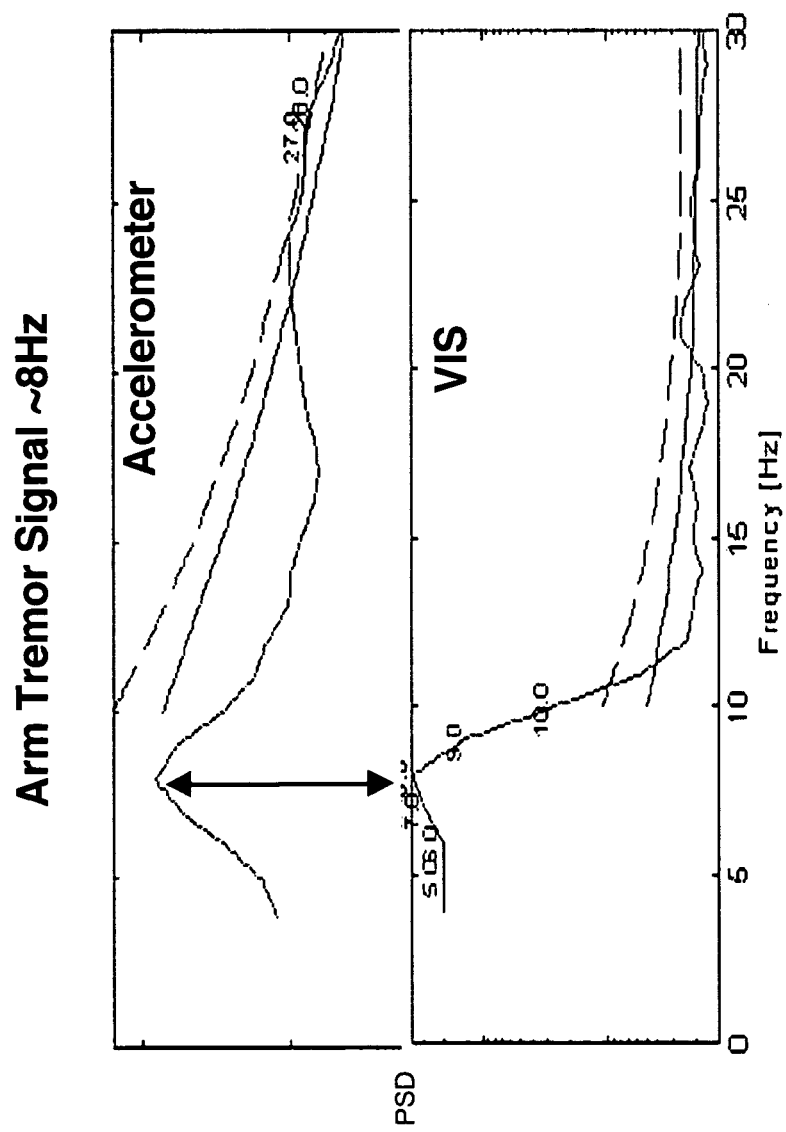
FIG. 24 shows a comparison of frequency responses obtained using a VIS according to the present invention and an accelerometer.

FIG. 24 shows the result of a Fast Fourier Transform performed on the collected data (contrast versus time), which compares frequency responses obtained from a VIS using the method according to the present invention and an accelerometer. Both demonstrate an ~8 Hz arm tremor signal.

Light amplitude modulation signals obtained from pixels may be further processed in order to better characterize the vibratory signals. For example, Fourier transform, wavelet analysis, and filtering may be used. In one embodiment, a matched filter technique is used to detect pulse. To construct a matched filter, the best pulse channel is taken from several different individuals, preferably at least five individuals. Next, the peak of each pulse is detected, and all pulses for an individual are averaged, giving an approximation of their pulse shape. The pulses for each individual are then normalized, both in frequency and amplitude, compared, and averaged to obtain a matched filter. This filter is then scaled to create a filter bank spanning the range of standard human pulse rates, e.g. about 40 to about 140 beats per minute (BPM).

Once the matched filter is obtained, each channel from a PDA is match filtered with the filter bank. Next, using the best-matched channel for each frequency, a set of approximately evenly spaced correlation peaks at the approximate target frequency is obtained. This gives the average pulse spacing, or BPM. Another matched filter at this detected frequency (BPM) can then be used to further refine the results.

INDUSTRIAL APPLICATIONS OF THE INVENTION

Examples of potential applications for the invention in medical/forensic fields is numerous. Methods according to the present invention can be used for:

- quantification of tremors or shaking due to Parkinson's disease or BET (benign essential tremor shaking) for drug development and clinical trials;
- non-contact monitoring of a patient's vital signs, such as respiration, pulse, normal tremors (both rate and amplitude)-especially useful for burn victims and battlefield triage;
- neonatal monitoring, where patients are small relative to conventional monitoring "patches";
- measurement of blood supply to skin graphs/flaps;
- provide feedback for tuning a brain or heart pacemaker;
- measurement of point-to-point relative phase or time-delay of blood flow;
- identification of arteries during minimally invasive "-scopic" surgery;
- detection of micro-expressions (eye motion, fidgeting, etc.) for non-contact lie detection of entire face or body.

These applications of the invention are all enabled by the full-image, non-contact nature of the invention, with its capability of pixel-by-pixel detection, processing and analysis. Other applications and advantages will be apparent based on the foregoing disclosure.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A method for detecting vibrations in a biological organism, comprising:

a) receiving a light signal from each of a plurality of regions of said biological organism at a corresponding plurality of light amplitude modulation detectors, wherein said light amplitude modulation detectors detect changes in the light amplitude of said light signal;
   b) generating from each of said received light signals a signal that is correlated to a vibration of the corresponding region;
   c) digitizing each of said correlated signals; and
   d) generating from said digitized signals an output representing said vibrations of said regions of said biological organism.

2. The method as set forth in claim 1, further comprising processing said digitized signals.

3. The method as set forth in claim 2, wherein said processing comprises executing a Fourier transform on said digitized signals, executing wavelet analysis of said digitized signals, or filtering said digitized signals.

4. The method as set forth in claim 3, wherein said filtering comprises match filtering.

5. The method as set forth in claim 1, further comprising optically filtering said received signals.

6. The method as set forth in claim 1, further comprising displaying a representation of said biological organism visually correlated with said generated signals representing said vibrations of said corresponding regions.

7. The method as set forth in claim 1, wherein said generating comprises generating a temporal spectral signal corresponding to the vibration of each corresponding region.

8. The method as set forth in claim 1, wherein said vibrations in said biological organism are generated from movement of biological fluids, air, organs, tissues, muscles, or body parts.

9. The method as set forth in claim 1, further comprising utilizing said output to detect or measure a property of said biological organism.

10. The method as set forth in claim 9, wherein said property is selected from the group consisting of heart rate, pulse rate, tremor, eye-blink rate, blood oxygen level, eye movement and blood flow.

11. The method as set forth in claim 1, wherein said biological organism is a mammal.

12. The method as set forth in claim 1, wherein said light signals comprise modulated light reflected from said biological organism.

13. The method as set forth in claim 12, said reflected light comprises light having a frequency in at least one of the visible light frequency range, the infrared frequency range, and the ultraviolet radiation range.

14. The method as set forth in claim 1, wherein said light signals comprise modulated light emitted from said biological organism.

15. The method as set forth in claim 14, wherein said emitted light comprises thermal infrared radiation or fluorescent radiation.

16. The method as set forth in claim 1, further comprising extracting from said received signals a representation of an oscillation of the corresponding regions.

17. The method as set forth in claim 16, wherein said extracting comprises removing from said received signals at least one component representing ambient radiation in a vicinity of said biological organism.

18. The method as set forth in claim 16, wherein said extracting comprises AC-coupling, high-pass temporal filtering, or DC-rejection of said received signals.

* * * * *